United States Patent [19]
Anderson et al.

[11] Patent Number: 5,968,738
[45] Date of Patent: *Oct. 19, 1999

[54] TWO-REPORTER FACS ANALYSIS OF MAMMALIAN CELLS USING GREEN FLUORESCENT PROTEINS

[75] Inventors: Michael T. Anderson, Menlo Park; Leonard A. Herzenberg, Stanford, both of Calif.

[73] Assignee: The Board of Trustees Of The Leland Stanford Junior University, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/761,771

[22] Filed: Dec. 6, 1996

Related U.S. Application Data

[60] Provisional application No. 60/008,232, Dec. 6, 1995.

[51] Int. Cl.$^6$ .............................. C12Q 1/68; C12Q 1/02; C12N 1/00; C12N 5/10
[52] U.S. Cl. ............................... 435/6; 435/29; 435/243; 435/325; 435/410
[58] Field of Search ................................. 435/4, 325, 6, 435/29, 243, 420

[56] References Cited

U.S. PATENT DOCUMENTS

| | | | |
|---|---|---|---|
| 5,070,012 | 12/1991 | Nolan et al. | 435/6 |
| 5,283,173 | 2/1994 | Fields et al. | 435/6 |
| 5,625,048 | 4/1997 | Tsin et al. | 536/23.4 |
| 5,777,079 | 7/1998 | Tsien et al. | 530/350 |

OTHER PUBLICATIONS

Marshall et al, Neuron, vol. 14: pp. 211–215 (Feb., 1995).
Rizzuto et al, Current Biology, vol. 5(6): pp. 635–642 (1995).
Bender, W. et al., Brighter GFP Mutant, Preprint available upon request to participants at the conference "Fluorescent Proteins and Applications" held Mar. 6–7, 1994 in Palo Alto, CA, pp. 1–6.
Ropp, J. Dezz et al.; Aequorea Green Fluorescent Protein Analysis by Flow Cytometry; Cytometry V21:309–317, 1995.
Cubitt, Andrew B. et al.; Understanding, Improving and Using Green Fluorescent Proteins; Elsevier Science Ltd.; pp. 448–455; 1995.
Heim, Roger et al.; Improved Green Fluorescence; Nature V373:663–664; Feb. 23, 1995.
Heim, Roger et al; Wavelength Mutations and Posttranslational Autoxidation of Green Fluorescent Protein; National Academy of Science USA; V91:12501–12504; Dec. 94.

*Primary Examiner*—Terry McKelvey
*Attorney, Agent, or Firm*—Bozicevic, Field & Francis LLP; Pamela Sherwood

[57] ABSTRACT

Two spectrally distinguishable GFPs are used as reporters in mammalian cells to simultaneously and independently analyze the expressions of two transcriptional elements. The two GFPs, encoded by single stably integrated transcriptional elements, are readily and quantitatively detectable by FACS or flow cytometry. One of the GFP mutants (S202F, T203I, V163A) retains only the major excitation peak of wild-type GFP, while the other (S65T, V163A) retains only the minor excitation peak of wild-type GFP. Both variants have emission peaks overlapping that of wtGFP. The first mutant is excited at 406 nm using a Kr ion laser, while the second mutant is excited at 488 nm using an Ar ion laser. Emissions from both GFPs are measured at about 515 nm. The mutant excited at 406 nm can be used in conjuction with a fluorescein-based assay such as FACS-Gal. Applications include drug screening, measurements of temporal orders of gene expression, analysis of signal transduction pathways, and measurements of protein-protein interactions using two-hybrid systems.

20 Claims, 9 Drawing Sheets

FIG. 1-A
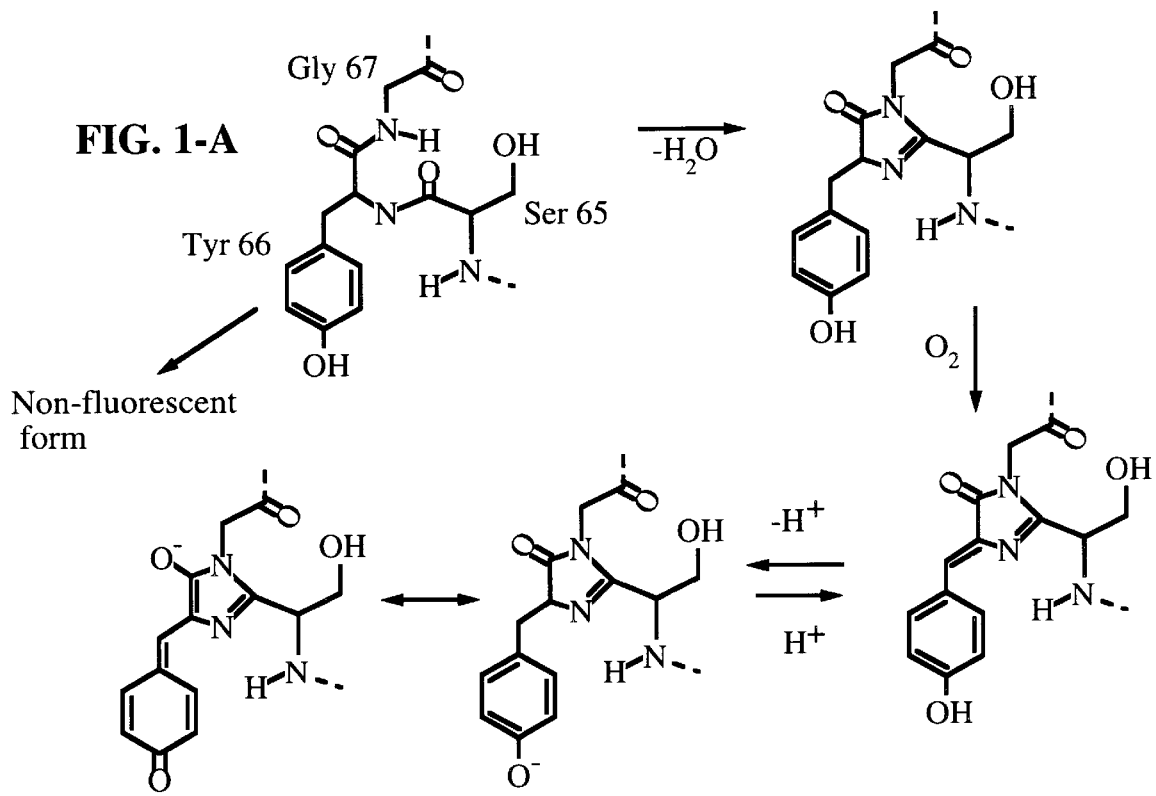
Non-fluorescent form
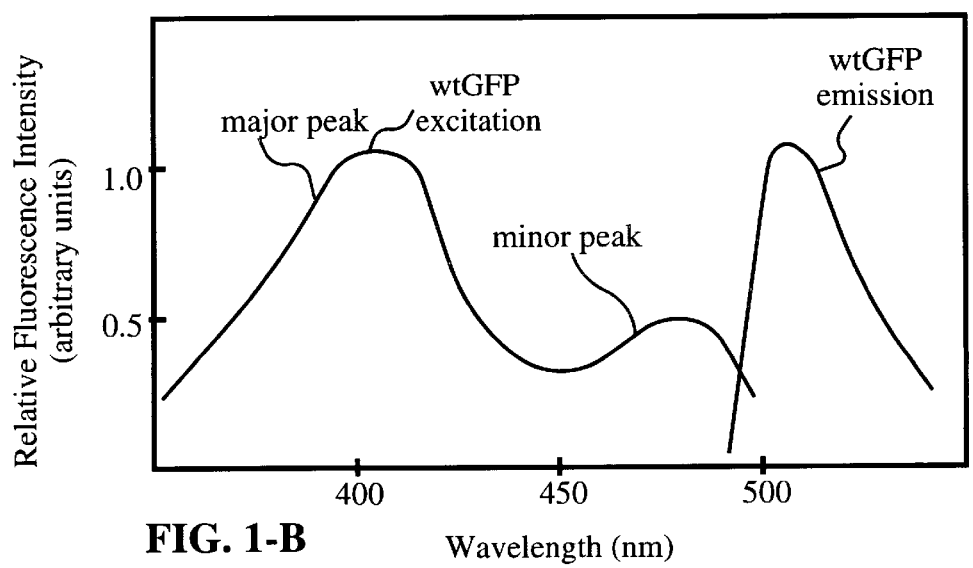
FIG. 1-B

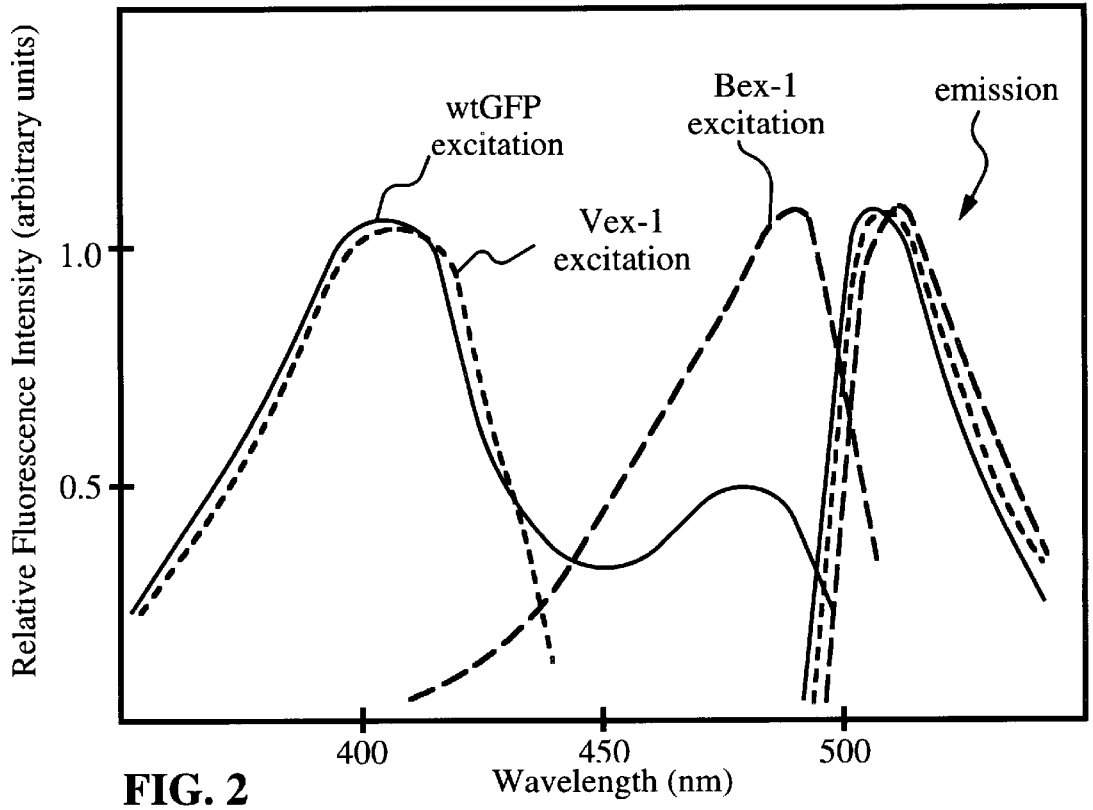
FIG. 2
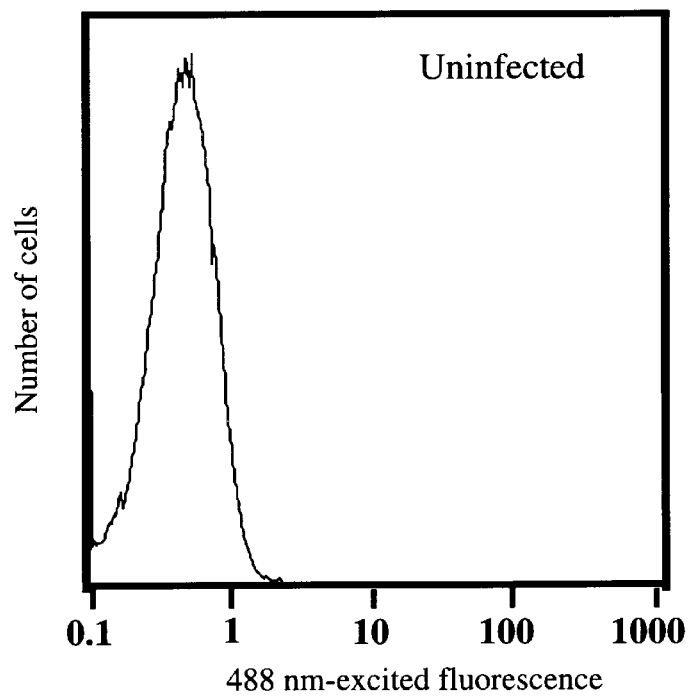
FIG. 4-A

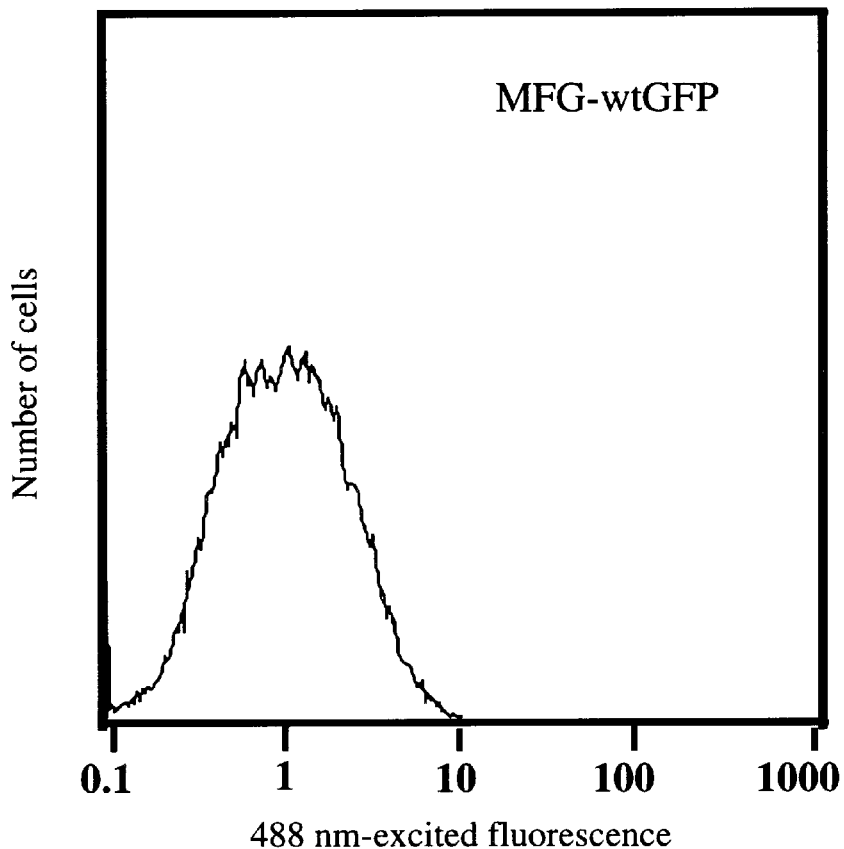
FIG. 4-B
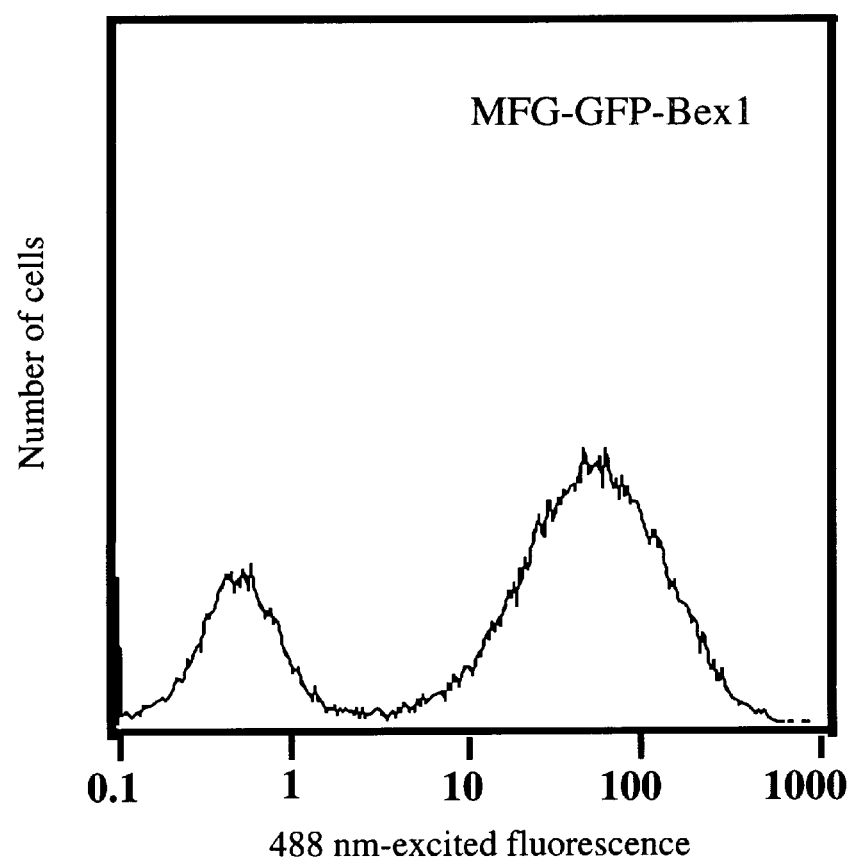
FIG. 4-C

FIG. 5-A
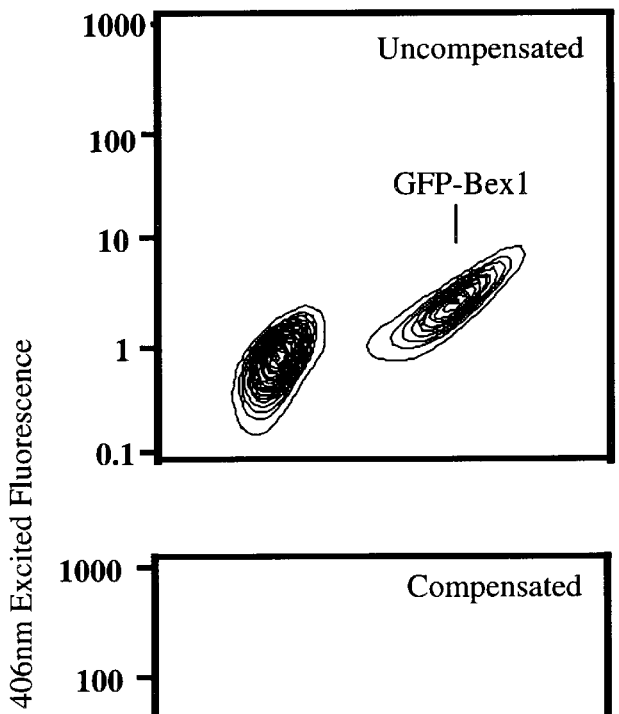
FIG. 5-B
FIG. 5-C
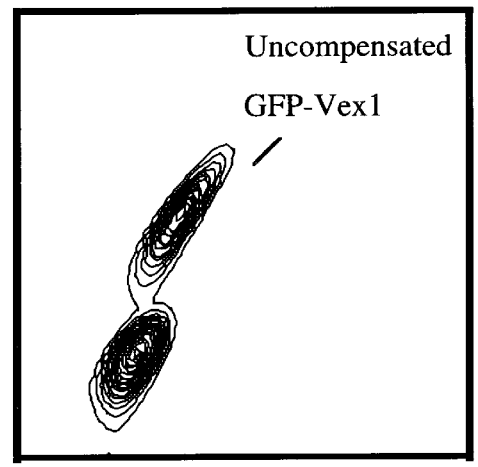
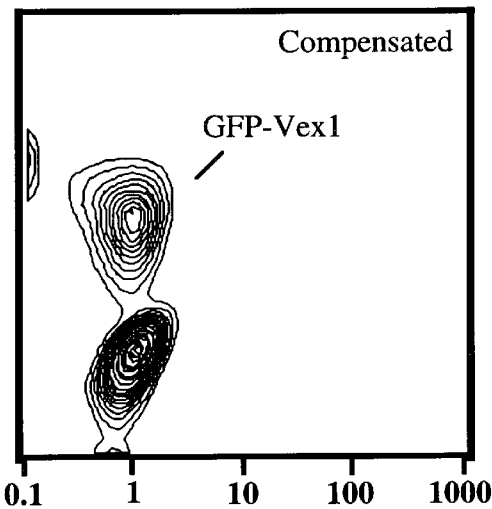
FIG. 5-D

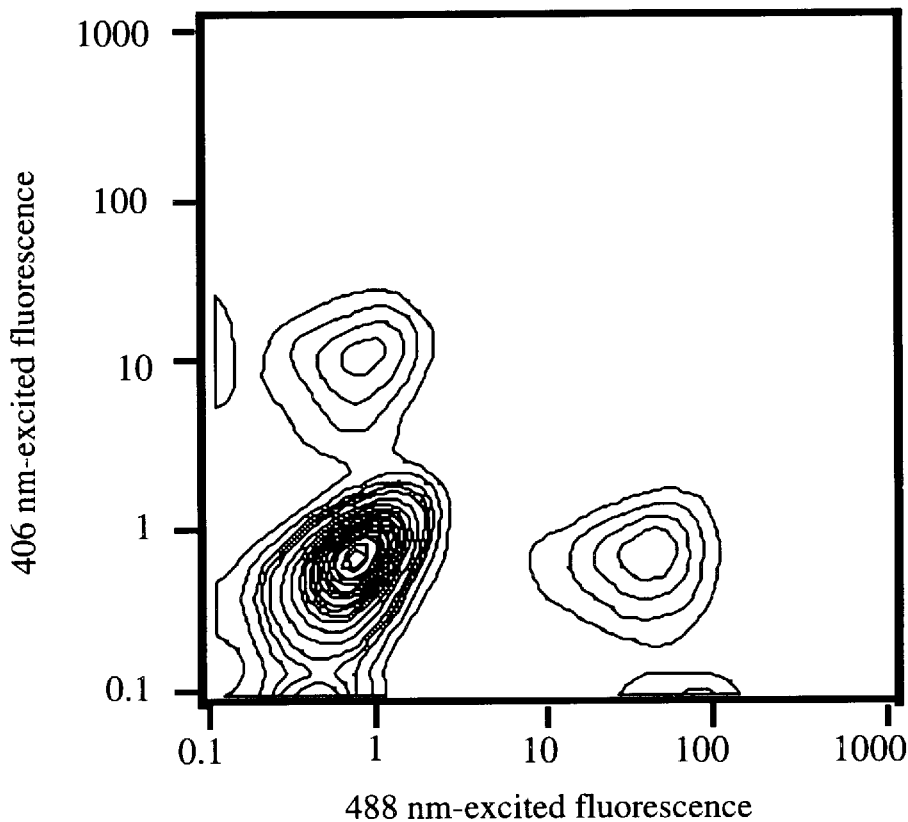
FIG. 6-A
0.06 MOI
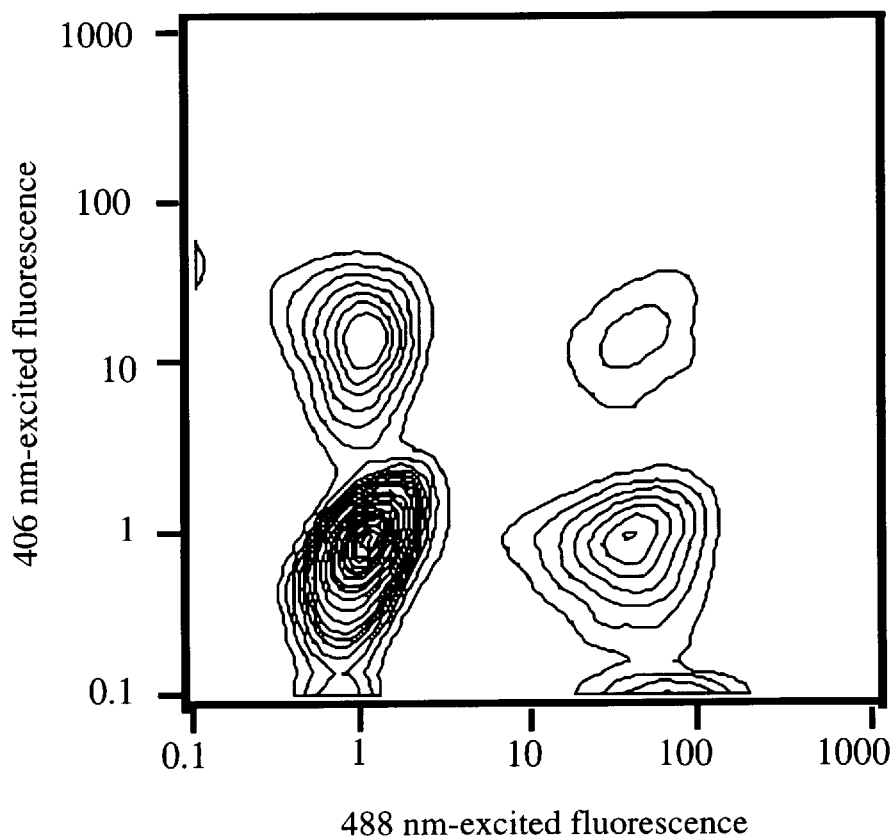
FIG. 6-B
0.13 MOI

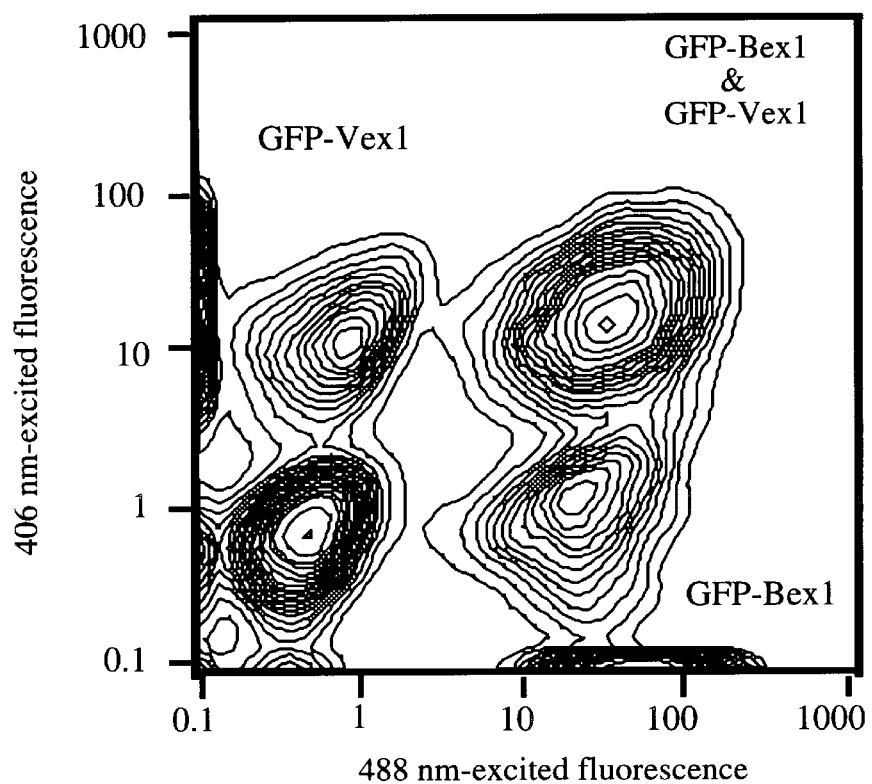
FIG. 6-C
0.65 MOI
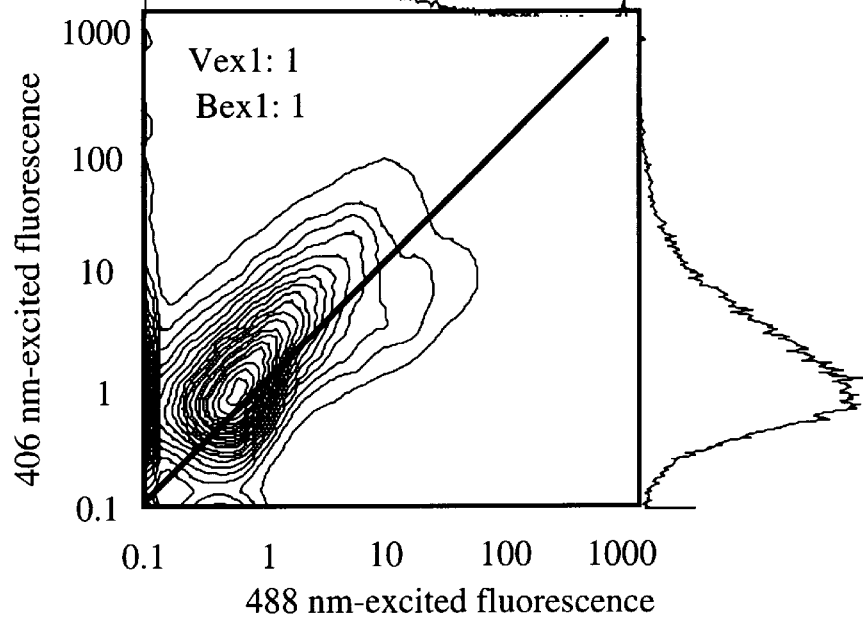
FIG. 7-A

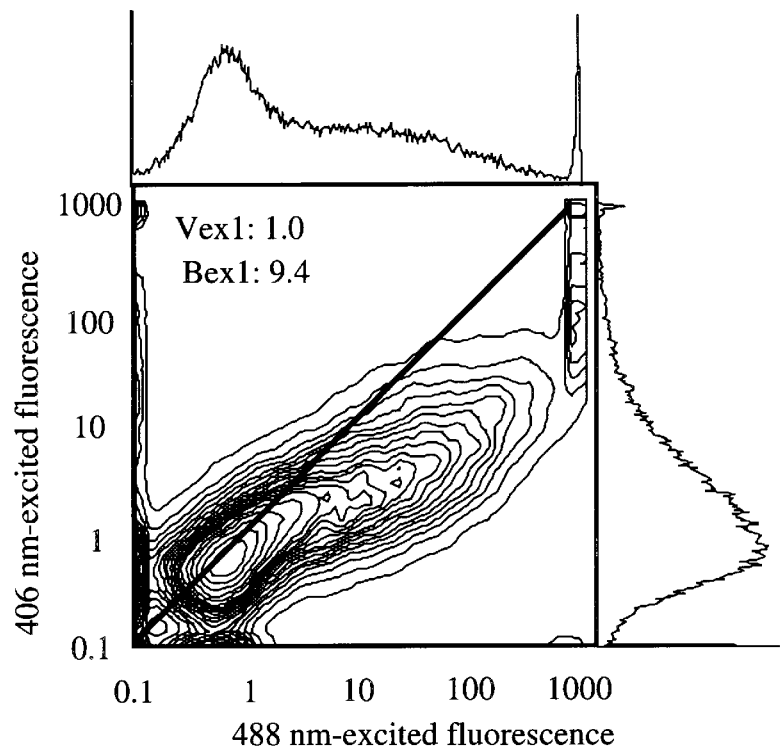
FIG. 7-B
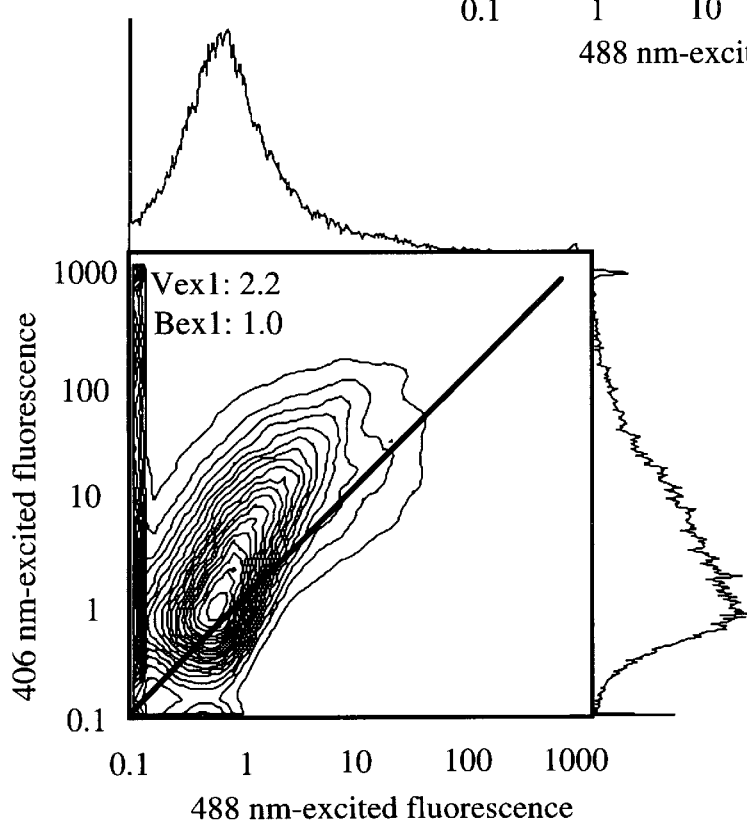
FIG. 7-C

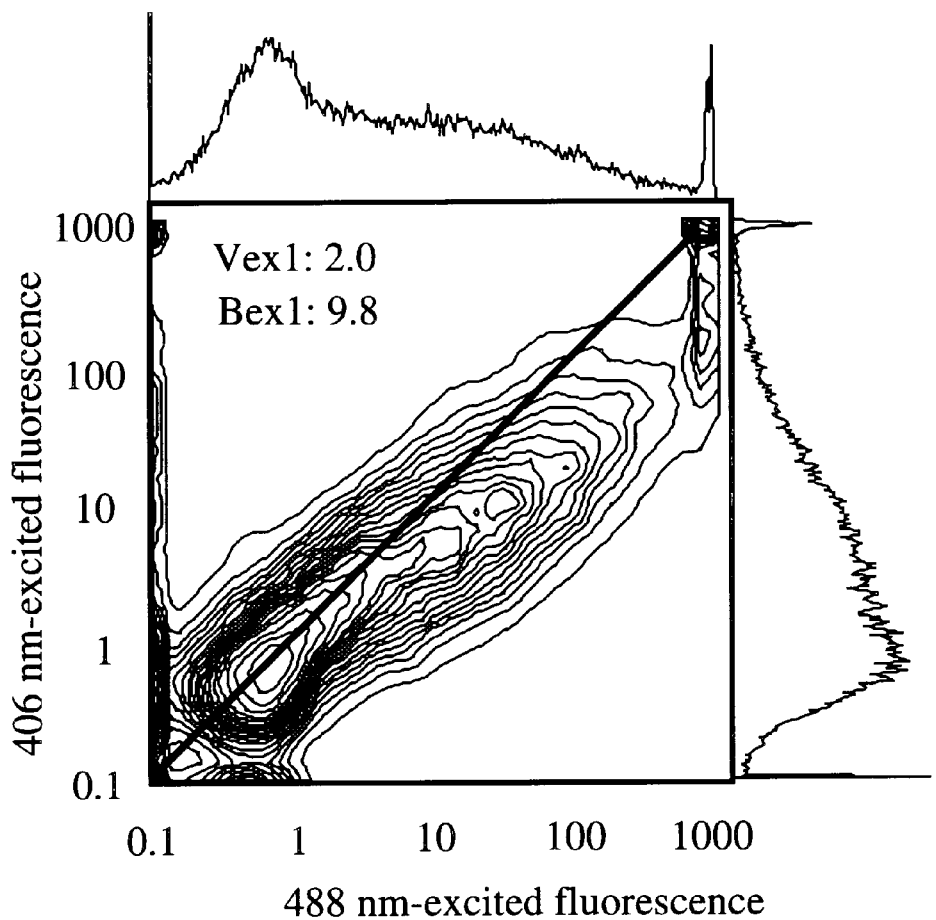
FIG. 7-D

TWO-REPORTER FACS ANALYSIS OF MAMMALIAN CELLS USING GREEN FLUORESCENT PROTEINS

CROSS-REFERENCES TO RELATED APPLICATIONS

This application claims the benefit of U.S. Provisional Application No. 60/008,232, filed Dec. 6, 1995, herein incorporated by reference.

This invention was made with U.S. Government support under Contract No. CA 42509, awarded by the National Institutes of Health. The U.S. Government has certain rights in this invention.

FIELD OF THE INVENTION

This invention relates to reporter genes for use in mammalian cells. More particularly, it relates to improved green fluorescent protein (GFP) mutants allowing independent, simultaneous analysis of two reporter genes in mammalian cells.

BACKGROUND OF THE INVENTION

Reporter/marker genes have found wide use in the study of cellular genetic regulation and gene function. In studies of genetic regulation, a regulatory element (e.g. promoter or enhancer) fused to a reporter gene is transfected into cells. The amount of reporter molecule subsequently generated reflects the transcriptional activity of the regulatory element.

Reporter genes can be used to measure, among others, transcriptional activities of synthetic enhancers (e.g. enhancers formed by multimerization of a single nuclear binding site motif), and protein-protein interactions using two-hybrid systems.

In studies of gene function, marker molecules distinguish cells expressing transfected/infected genes from uninfected cells. A gene of interest is co-transfected with a marker gene. Cells expressing the gene of interest are identified by the presence of marker molecule. The marker molecule and the product of interest can be expressed as a protein fusion. Alternatively, the marker molecule and the product of interest can be expressed as distinct proteins from a transcriptional fusion having an internal ribosomal entry site (IRES).

With the recent development of reporter genes detectable by flow cytometry, it has become possible to analyze the expression of a transcriptional element within an individual mammalian cell. However, there is no currently available method of independently analyzing two transcriptional elements within a mammalian cell.

The articles by Nolan et al. in *PNAS USA* 85:2603–2607 (1985) and Fiering et al. in *Cytometry* 12: 291–301 (1991), herein incorporated by reference, describe FACS-Gal, a fluorogenic assay that permits the detection and isolation of individual cells expressing lacZ. The gene lacZ encodes the enzyme β-galactosidase, which cleaves the non-fluorescent substrate fluorescein-di-β-galactopyranoside to release fluorescein. For further information on FACS-Gal and some of its uses, see also the article by Kerr and Herzenberg in *Methods: A Companion to Methods in Enzymology* 2(3):261–271 (1991), herein incorporated by reference.

Another type of reporter gene previously used for FACS analysis of mammalian cells is described in an article by Rice et al. in *PNAS USA* 89(12):5467–5471 (1992). A gene encoding a plasma membrane surface receptor is transfected into cells that do not endogenously express the receptor. Fluorochrome-conjugated antibodies bind to receptor present on the cell surface, and can be detected by flow cytometry. Several difficulties have precluded the widespread use of receptor-encoding reporter genes, including the unquantitative nature of the detection, and the potential interference of the receptor with normal signal transduction pathways.

Recently, the green fluorescent protein (GFP) gene, isolated from the jellyfish *Aequorea victoria*, has become available as a potential reporter or marker in procaryotes and eucaryotes. The gfp gene encodes a protein which fluoresces when excited by violet or blue-green light. GFP is unique among reporters in that the GFP fluorophore spontaneously forms intracellularly without added cofactors, and in that it provides a direct readout of gene expression. The use of GFP eliminates the need for introducing a substrate into live cells, and for evaluating complex enzyme-substrate kinetics. For information on GFP see for example U.S. Pat. No. 5,491,084, herein incorporated by reference, and the articles by Peters et al. in *Dev. Biol.* 171:252–257 (1995), Rizzuto et al. in *Curr. Biol.* 5:635–642 (1995), and Cubitt et al. in *Trends in Biochemical Sciences* 20:448–455 (1995). The Cubitt et al. article includes a summary of reports of GFP expression in various procaryotic and eucaryotic systems.

GFP is a 238-amino acid protein, with amino-acids 65–67 (Ser, Tyr, and Gly, respectively) thought to be involved in the formation of the chromophore. For information on the structure of wtGFP, see the article by Yang et al. in *Nature Biotechnology* 14(10):1246–1251 (1996). FIG. 1-A shows a proposed biosynthetic scheme for the GFP chromophore. Only some of the expressed protein folds into a fluorescent form. For a given quantity of GFP within a cell, the GFP brightness depends on the quantum yield of the protein and on the fraction of protein correctly folded.

FIG. 1-B shows the excitation and emission spectra of wtGFP. Wild-type GFP has a major excitation peak at 395 nm, a minor excitation peak at 475 nm and a single emission peak at 509 nm. The two excitation peaks presumably reflect two distinct states (protonated and unprotonated) of the fluorophore. Illumination of wtGFP with UV or violet light results in photobleaching, and in photoisomerization from the state maximally excited at 395 nm to the state maximally excited at 475 nm. Photobleaching decreases the absolute magnitude of both excitation peaks, while photoisomerization reduces the relative magnitude of the major excitation peak. For data on photobleaching and photoisomerization of GFP, see the above-incorporated article by Cubitt et al.

A number of GFP mutants having altered excitation and emission spectra when expressed in *E. coli* are described in articles by Heim et al. in *PNAS USA* 91:12501–12504 (1994) and in *Nature* 373:663–664 (1995), herein incorporated by reference. Table 1 provides a summary of some characteristics of GFPs expressed in *E. coli*, as disclosed in the two Heim et al. articles.

TABLE 1

| Mutation | Excitation maximum | Emission maximum | Relative fluorescence (%) |
|---|---|---|---|
| None | 396 nm | 508 nm | =100 |
| Ser-202 to Phe Thr-203 to Ile | 398 nm | 511 nm | 117 (w/395 nm exc) |
| Ile-167 to Val | 471 nm | 502 nm | 166 (w/475 nm exc) |
| Ile-167 to Thr | 471 nm | 502 nm | 188 (w/475 nm exc) |
| Tyr-66 to His | 382 nm | 448 nm | 57 (w/395 nm exc) |
| Tyr-66 to Trp | 458 nm | 480 nm | Not done |
| Ser-65 to Thr | 489 nm | 511 nm | ~600 |
| Ser-65 to Cys | 479 nm | 507 nm | ~600 |

Wild-type GFP as well as GFP mutants of various colors can be readily and quantitatively detected in bacteria, by fluorescence microscopy or flow cytometry. In mammalian cells, however, analysis of GFP fluorescence has proven relatively difficult, primarily because of the relatively high levels of autofluorescence in mammalian cells, and the high temperatures at which mammalian cells are grown. Molecules such as pyridine nucleotides, flavin nucleotides and flavoproteins fluoresce upon ultraviolet or blue excitation, and can obscure GFP fluorescence. Mammalian cell autofluorescence is particularly bright for UV excitation. Moreover, mammalian cells are typically grown at 37° C., well above the temperature that yields maximal GFP fluorescence. The high temperatures at which mammalian cells are grown hinder the proper folding of GFP. For information on the temperature dependence of GFP fluorescence, see the article by Ogawa et al. in *PNAS USA* 92:11899–11903 (1995), herein incorporated by reference.

Wild-type or S65T GFP fluorescence can be qualitatively detected by flow cytometry in transiently transfected mammalian cells containing multiple copies of GFP expression vectors (data not shown, also reported in the article by Ropp et al. in *Cytometry* 21:309–317 (1995), herein incorporated by reference). However, the relative dullness of GFP in mammalian cells and the spectral overlap of wtGFP with available mutants have impeded the simultaneous detection by flow cytometry of multiple GFPs within an individual mammalian cell.

Ropp et al. describe an analysis by spectrofluorometry and flow cytometry of mammalian cells expressing wtGFP or S65T-GFP. The article also contains data on green autofluorescence for UV, violet, and blue green excitation in mammalian cells. The dullness of the described GFPs, and the similarity of the responses of wtGFP to blue and violet excitation would preclude the simultaneous flow cytometry analysis of wtGFP and S65T-GFP in mammalian cells. The two variants could not be used to distinguish cells expressing a single GFP variant from cells expressing both variants. Also, the two variants could not be used to independently analyze the expression of two transcriptional elements within mammalian cells.

Bender et al. (Bender, Kahana, Hudson, and Silver, personal communication) have isolated a number of mutants that show increased fluorescence in *E. coli*. In particular, one of the mutants (V163A) identified by Bender et al. retains the spectral properties (wavelengths of the excitation and emission peaks) of wild-type GFP but shows a 17-fold increase in fluorescence intensity in *E. coli*.

OBJECTS AND ADVANTAGES OF THE INVENTION

Accordingly, it is a primary object of the present invention to provide two reporter genes independently detectable by flow cytometry in a mammalian cell. It is another object to provide a method of simultaneously detecting the expression products of two independent transcriptional elements in a mammalian cell. The reporter genes do not require substrates or exogenous cofactors for detection of their products. It is a further object of this invention to provide two spectrally distinguishable GFPs detectable in mammalian cells. The fluorescence signals from the GFPs are significantly higher than cell autofluorescence signals, such that a population of cells expressing either of the two GFPs is distinguishable from a population of background cells. It is still another object to provide GFPs with sufficiently low intersignal crosstalk to permit distinguishing cells expressing both GFPs from cells expressing only one of the GFPs. The excitation spectra of the two GFPs are matched to available laser lines. The excitation spectrum of each of the two GFPs is similar to one of the excitation peaks of wtGFP. The emission spectra of the two GFPs are similar to the emission spectrum of the wild-type protein. The two GFPs are structurally similar and have similar brightness and expression levels for a given controlling regulatory element, allowing direct comparisons of transcriptional activities for different regulatory elements. The two mutants fold more efficiently, and have better quantum yields than available UV-excited GFP variants. It is another object of this invention to provide a method of quantitatively analyzing the expression of two transcriptional elements within a mammalian cell. The detected fluorescence signals provide direct measures of the expression levels of corresponding transcriptional elements, and do not need to be interpreted in light of complex enzyme-substrate kinetics.

SUMMARY OF THE INVENTION

The invention provides bright, spectrally separated GFP variants allowing simultaneous flow cytometry analyses of two transcriptional elements within mammalian cells. Each of the two GFPs has a single excitation peak. The excitation peak of one of the GFPs matches the major excitation peak of wtGFP, while the excitation peak of the other GFP approximately matches the minor excitation peak of wtGFP. The present invention allows distinguishing cells expressing distinct GFPs from background cells. The strategies of distinguishing the two GFPs by excitation wavelengths and of using GFPs that retain one of the excitation peaks of wtGFP allow the use of relatively bright variants for dual-reporter analyses, since the GFPs are well matched to available bright light sources, do not require UV excitation, and have reduced intersignal crosstalk.

DESCRIPTION OF THE FIGURES

FIG. 1-A illustrates a proposed biosynthetic scheme for the wtGFP chromophore.

FIG. 1-B shows the excitation and emission spectra of wtGFP.

FIG. 2 shows the excitation and emission spectra of two GFP mutants of the present invention.

FIG. 4-A shows a 488 nm FACS scan of uninfected NIH/3T3 cells.

FIG. 4-B shows a 488 nm FACS scan of NIH/3T3 cells transfected with a single copy of wtgfp per cell.

FIG. 4-C shows a 488 nm FACS scan of NIH/3T3 cells transfected with a single copy of bex-1 per cell, according to the present invention.

FIG. 5-A shows a dual-excitation FACS scan of bex-1-transfected NIH/3T3 cells, without fluorescence compensation, according to the present invention.

FIG. 5-B shows a dual-excitation fluorescence-compensated FACS scan of bex-1-transfected NIH/3T3 cells, according to the present invention.

FIG. 5-C shows a dual-excitation FACS scan of vex-1-transfected NIH/3T3 cells, without fluorescence compensation, according to the present invention.

FIG. 5-D shows a dual-excitation fluorescence-compensated FACS scan of vex-1-transfected NIH/3T3 cells, according to the present invention.

FIG. 6-A shows a dual-excitation FACS scan of NIH/3T3 cells transfected with bex-1 and vex-1 at a multiplicity of infection of 0.06, according to the present invention.

FIG. 6-B shows a dual-excitation FACS scan of NIH/3T3 cells transfected with bex-1 and vex-1 at a multiplicity of infection of 0.13, according to the present invention.

FIG. 6-C shows a dual-excitation FACS scan of NIH/3T3 cells transfected with bex-1 and vex-1 at a multiplicity of infection of 0.65, according to the present invention.

FIG. 7-A shows a FACS scan of BOSC 23 cells transfected with bex-1 and vex-1, in the absence of induction of the two reporter genes, according to the present invention.

FIG. 7-B shows a FACS scan of BOSC 23 cells transfected with bex-1 and vex-1, under inducing conditions for bex-1 but not vex-1, according to the present invention.

FIG. 7-C shows a FACS scan of BOSC 23 cells transfected with bex-1 and vex-1, under inducing conditions for vex-1 but not bex-1, according to the present invention.

FIG. 7-D shows a FACS scan of BOSC 23 cells transfected with bex-1 and vex-1, under inducing conditions for both vex-1 and bex-1, according to the present invention.

DETAILED DESCRIPTION

Figure 3:
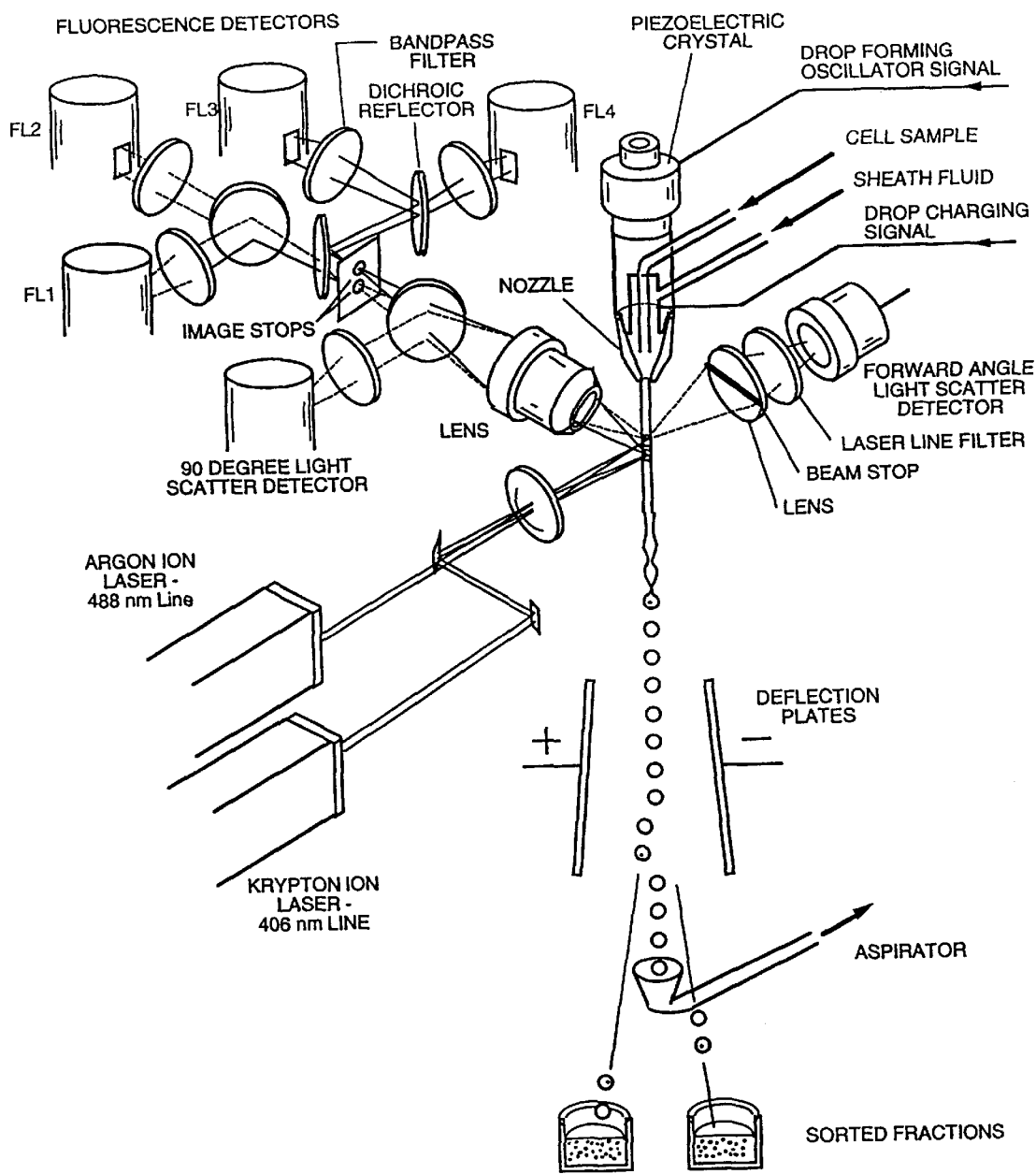
FIG. 3 is a schematic view of a fluorescence activated cell sorter suitable for use in a method of the present invention.

The statement that a gene is used as a reporter gene in a cell is understood to mean that level of a product of the gene is used to provide a measurement of a transcriptional activity of the gene. The statement that a gene is used as a marker gene in a cell is understood to mean that a detection of a product of the gene is used to determine whether the gene is present or expressed in the cell. The term background cell is understood to refer to a cell that does not significantly express a gene product under analysis. The statement that two peaks overlap is understood to mean that the wavelength ranges defined by the full-widths-at-half-maxima of the two peaks overlap. The statement that a wavelength is within a peak is understood to mean that the wavelength is within the range defined by the full-width-at-half-maximum of the peak. The statement that a signal is measured at a wavelength is understood to mean that the wavelength is within the full-width-at-half-maximum of an emission filter used for the measurement.

The present invention provides a method of analyzing mammalian cells, preferably by flow cytometry. Each cell comprises a first transcriptional element and a second transcriptional element. The method comprises measuring a first fluorescence signal from a first intracellular expression product of the first transcriptional element, and a second fluorescence signal from a second intracellular expression product of the second transcriptional element. Cells expressing the transcriptional elements can be distinguished and sorted from background mammalian cells according to either of the signal(s).

Preferably, the expression products comprise spectrally distinguishable green fluorescent proteins encoded by the corresponding transcriptional elements. Alternatively, one of the transcriptional elements encodes an enzyme capable of releasing the corresponding expression product by cleaving a non-fluorescent precursor of the expression product.

In a preferred embodiment, the first green fluorescent protein has a set of first spectral optimization mutations (S202F, T203I) and a first stability mutation (V163A), while the second green fluorescent protein has a second spectral optimization mutation (S65T) and a second stability mutation (V163A). The spectral optimization mutations match the excitation spectra of the two proteins to desired excitation wavelengths (available laser lines), and reduce the spectral overlap between the two proteins. The stability mutations improve the stability, and thus brightness, of the two proteins.

The first GFP has a single excitation peak that overlaps the major excitation peak of wtGFP, and does not overlap the minor excitation peak. In particular, the excitation peak of the first GFP substantially coincides with the major excitation peak of wtGFP. The second GFP has a single excitation peak that overlaps the minor excitation peak of wtGFP, and does not overlap the major excitation peak. The excitation peak of the second GFP is preferably shifted away from the excitation peak of the first GFP, so as to reduce the spectral overlap between the two GFPs. The two GFPs have distinguishable excitation peaks. The emission peaks of both GFPs overlap the emission peak of wtGFP. In particular, the emission spectra of the two GFPs coincide with that of wtGFP. The GFPs are distinguished according to wavelengths of light incident on the cell under analysis.

The use of mutants having excitation spectra matching only one of the wtGFP excitation peaks eliminates the need for UV excitation of the cell, as compared to the commonly used approach of using GFPs distinguishable by color. No GFP variant with an emission peak at a wavelength significantly higher than that of the wtGFP emission peak has been developed so far. Distinguishing two GFPs by color thus requires the use of a mutant having an emission peak significantly lower in wavelength than 500 nm, such as Y66H (see Table 1). The Y66H variant requires UV excitation, however. Also, GFPs that are structurally similar to wtGFP in one of its conformations (protonated or unprotonated) have been empirically observed to be brighter than UV-excited variants.

The cell is first illuminated at a wavelength $\lambda_{ex}[1]$ within the excitation peak of the first protein. The response of the second GFP to light of wavelength $\lambda_{ex}[1]$ is minimal relative to that of the first GFP. Consequently, the fluorescence signal resulting from excitation at $\lambda_{ex}[1]$ measures substantially the response of the first GFP. The cell is then illuminated at a wavelength $\lambda_{ex}[2]$ within the excitation peak of the second protein. The response of the first GFP to light of wavelength $\lambda_{ex}[2]$ is minimal relative to that of the second GFP. Thus, the fluorescence signal resulting from excitation at $\lambda_{ex}[2]$ measures substantially the response of the second GFP. The low overlap between the excitation spectra of the two mutants allows adequate compensation of the first signal for the level of second protein, and of the second signal for the level of first protein.

Preferably, a Kr ion laser is used for generating light of wavelength $\lambda_{ex}[1]=406$ nm, and an Ar ion laser for generating light of wavelength $\lambda_{ex}[2]=488$ nm. The first signal is measured at a wavelength $\lambda_{em}[1]$ between 500 nm and 540 nm, and the second signal is measured at a wavelength $\lambda_{em}[2]$ between 500 nm and 540 nm. Preferably, bandpass 515±20 nm emission filters are used for detecting both fluorescence signals.

Each transcriptional element comprises a regulatory element (such as a promoter, enhancer, or repressor) operatively connected to a coding portion encoding a GFP. The regulatory element regulates the expression of the coding portion. The transcriptional elements are preferably stably integrated into the genomes of the host cells. Each GFP is detectable by flow cytometry when encoded by a single expressed copy of a corresponding transcriptional element.

Applications of the present invention include sorting cells carrying a particular combination of genes of interest, simultaneously screening agents for effects on multiple regulatory elements, and studying protein-protein interactions using two-hybrid systems. In drug screening applications, the transcriptional elements are exposed to a molecule of interest. The fluorescence signals then measure the effects of the molecule of interest on the transcriptional elements. Cells displaying predetermined fluorescence levels are selected by FACS or high-throughput screening methods.

In a two-hybrid system used for the study of protein-protein interactions, a first protein of interest is conjugated to a DNA-binding domain, while a second protein of interest is conjugated to a transcription activation domain. The DNA-binding domain is capable of binding to a regulatory element of each transcriptional element, while the transcription activation domain is necessary for the transcription of the transcriptional element. The transcriptional element is only expressed when the DNA-binding domain and the transcription activation domain are in proximity. The signal from the GFP encoded by a transcriptional element measures the binding of the first protein of interest to the second protein of interest. For detailed information on two-hybrid systems, see the article by Fearon et al. in *PNAS USA* 89:7958–7962 (1992), herein incorporated by reference.

The present invention provides a method of independently analyzing by flow cytometry the expression levels of two transcriptional elements in a mammalian cell, by measuring fluorescence signals from proteins encoded by the transcriptional elements.

To establish a pair of FACS-analyzable reporter molecules, two of the GFP variants identified by Heim et al. in *E. coli* (see Table 1) were modified so as to allow mammalian cell analysis. The S65T (Heim et al.) mutant retains the minor excitation peak of wtGFP, but lacks the major excitation peak of wtGFP. For detailed information on the S65T mutant, see the article by Ormo et al. in *Science* 273: 1392–1395 (1996). The (S202F, T203I) (Heim et al.) variant lacks the minor excitation peak of wtGFP, but retains the major excitation peak of GFP. Presumably, the S65T mutation favors one state (protonated or unprotonated) of the chromophore, while the (S202F, T203I) mutations favor the other state.

The S65T and (S202F, T203I) mutants cannot be used effectively in mammalian cells because of their relative dullness. Surprisingly, it was found that adding the V163A mutation identified by Bender et al. to the S65T and (S202F, T203I) mutations does not affect the spectral properties of the target GFPs, but significantly increases their stability. The excitation and emission spectra of the S202F, T203I, V163A (named Vex-1, or Violet-Excited-1), and S65T, V163A (named Bex-1, or Blue-Excited-1) mutants are shown in FIG. 2. Each peak in FIG. 2 is normalized individually.

Presumably, the V163A mutation improves the stability of GFP in mammalian cells. The effect of adding the V163A mutation to the variants identified by Heim et al. is not a priori predictable; other mutations identified by Bender et al. do not have the same effect as V163A. Both Bex-1 and Vex-1 are bright enough to allow distinguishing cells expressing a single copy of bex-1 or vex-1 from background cells. The Vex-1 and Bex-1 variants do not photoisomerize upon excitation at 406 nm and 488 nm, respectively.

The excitation spectra of the Vex-1 and Bex-1 mutants match, respectively, the 406 nm line of Kr ion lasers and the 488 nm line of Ar ion lasers. Krypton and argon ion lasers are available for use with conventional FACS equipment. Vex-1 and Bex-1 are spectrally distinguishable by their excitation peaks, but not by their emission peaks (colors). The two mutants have high quantum efficiencies, and fold relatively efficiently. Moreover, the two mutants do not require UV excitation.

The low spectral overlap between Bex-1 and Vex-1 is critical for their simultaneous detection. The low spectral overlap permits distinguishing between the signals from the two variants. The low spectral overlap is also important for allowing the use of fluorescence compensation for generating corrected signals, since the accuracy of fluorescence compensation decreases rapidly with intersignal crosstalk. For high crosstalk, fluorescence compensation loses its usefulness, as small variations in the level of one protein can entirely obscure the signal from the other protein.

Preferably, the codons of the two transcriptional elements are optimized for mammalian expression. The coding portions of the transcriptional elements consist substantially of codons commonly used in mammalian cells, as described in the article by Crameri et al., *Nature Biotechnology* 14(3):315–319 (1996), herein incorporated by reference.

The cell is preferably run through a two-laser fluorescence activated cell sorter. FIG. 3 shows schematically the design of a fluorescence activated cell sorter suitable for use with the present invention. Briefly, light at two different wavelengths is incident on the cell stream at distinct locations, and is incident on a given cell at distinct times. Each location corresponds to a distinct light path to a corresponding light detector, and thus fluorescence emitted from a cell as a result of excitation at one wavelength is distinguishable from fluorescence emitted by the same cell following excitation at the other wavelength.

In a preferred embodiment, a cell containing Bex-1 and Vex-1 is illuminated at a first location at $\lambda_{ex}[1]$=406 nm, using a Kr ion laser. The fluorescence signal resulting from the 406 nm illumination is measured at a first detector using a 515±20 nm emission filter. The cell is illuminated at a second location at a wavelength $\lambda_{ex}[2]$=488 nm, using a Ar ion laser. The fluorescence signal resulting from the 488 nm illumination at $\lambda_{ex}[2]$ is measured at is measured at second detector using a 515±20 nm emission filter. The cell is then sorted according to the first and second signals.

The following examples are intended to illustrate the present invention, and should not be construed to limit the scope of the present invention.

EXAMPLE 1
Plasmids, Mutagenesis, and Sequencing

A MFG-wtgfp-pBR322 plasmid was mutagenized by PCR to generate mutants of the present invention. A PCR-based site-directed mutagenesis scheme, as described in the article by Picard et al. in *Nucleic Acids Res.* 22:2587–2591 (1994), herein incorporated by reference, was used to generate bex-1 and vex-1. A Qiaquick Spin PCR Purification (Qiagen, Chatsworth, Calif.) step was added following the generation of the megaprimer. The coding portions of the two GFP variants from MFG-bex-1 and MFG-vex-1 were cloned into XbaI-HindIII digested pGL3 (Promega) to create pGL3-bex-1 and pGL3-vex-1. The HindIII-SacI fragment of pOPRSV1-CAT (Stratagene) containing the lac operator (lacO) and RSV promoter was inserted into pGL3-vex-1 upstream of the gfp coding portion to create the lac inducible construct pGL3-OPRSV1-vex-1. The lac repressor expression vector p3'SS and the tet repressor-vp16 chimera expression vector pUHD15-1 were obtained from Stratagene. The gfp coding regions were sequenced by DyeDeoxy Terminator Cycle Sequencing (PRISM Ready Reaction Kit, Perkin Elmer, Foster City, Calif.). DNA sequence analysis was performed with Intelligenetics Inc. (Mountain View, Calif.) software.

EXAMPLE 2
Cells, Tissue Culture and Retroviral Infection

NIH/3T3 cells (ATCC CCL 163), BOSC 23 and Phoenix retroviral producer cells (G. Nolan, unpublished) were maintained as described in the article by Pear et al. in *PNAS USA* 90:8392–8396 (1993), herein incorporated by reference. Transfection of BOSC 23 and Phoenix producer cells, as well as retroviral infection of 3T3 cells were performed as described in the above-incorporated article by Pear et al. For gene induction experiments, BOSC 23 cells were maintained in 1 μg/ml tetracycline (tet) (obtained from Sigma) for 24 hours and then transfected in the continued presence of tet. After 24 hours, cells were harvested, split into four aliquots, and incubated for 48 hours in the presence or absence of 1 μg/ml tet and/or 50 m isopropylthio-β-D-galactoside (IPTG) (Life Technologies).

EXAMPLE 3

FACS Analysis

FACS analyses were carried out on a two-laser FACStar Plus platform (Becton Dickinson) modified by the Stanford FACS Development Group. An Innova 302 Krypton ion laser (Coherent Inc., Santa Clara, Calif.) tuned to 406 nm, and an Argon ion laser (Coherent Inc.) tuned to 488 nm were used in the dual laser experiments. To optimize the detection of GFP fluorescence, the standard fluorescein filter was replaced with a 515/40 nm interference filter. A detector with a 630/30 nm bandpass filter was used for autofluorescence compensation, as described in the article by Alberti et al. in *Cytometry* 8:114 (1988)). The two laser-stream intercepts were spatially separated, as were the two paths of light emitted by each GFP, as illustrated in FIG. 3. Identical emission filters were used for the two detectors. Multiparameter data were collected and analyzed using the FACS-DESK program, configured as described by Moore and Kautz in *The Handbook of Experimental Immunology*, eds. Weir et al., Blackwell Scientific, Edinburgh, pages 30.1–30.11.

EXAMPLE 4

Uninfected NIH/3T3 cells were analyzed by FACS using 488 nm excitation. Light was collected at 495–535 nm. FIG. 4-A shows the number of cells as a function of fluorescence intensity.

A MFG-wtgfp construct was stably incorporated into NIH/3T3 cells by retroviral gene transfer, as described in the above-incorporated article by Pear et al. in *PNAS USA* 90:8392–8396 (1993). Cells were analyzed by FACS 48 hours after infection, in a manner similar to that described above for uninfected cells. FIG. 4-B illustrates the resulting FACS scan. While the median fluorescence of the MFG-wtgfp-infected population is 2-fold greater than that of uninfected cells, the difference in fluorescence does not permit distinguishing the populations of infected and background cells.

A MFG-bex-1 construct was stably incorporated into NIH/3T3 cells under conditions yielding infection efficiencies comparable to those achieved with MFG-wtgfp. A FACS scan of the cells revealed distinguishable infected and background populations, as illustrated in FIG. 4-C. The median fluorescence of the infected population was approximately 50-fold greater than that of the background population, or 25-fold greater than the median fluorescence of the MFG-wtgfp population. The infected population consisted of 60% of the total population. Assuming the number of viral integrants per cell followed a Poisson distribution, the probability of an infected cell carrying a single copy of gfp was approximately 0.36. The infected cells are clearly distinguishable from the background cells.

EXAMPLE 5

NIH/3T3 cells were infected with MFG-bex-1 at a multiplicity of infection (MOI) five times lower than that used in Example 4. The cells were analyzed in a cell sorter similar to that shown in FIG. 3. The resulting FACS scan is illustrated in FIG. 5-A. Infected cells fluoresced 40 times brighter than background cells upon 488 nm excitation, and 3 times brighter than background cells upon 406 nm excitation. Software compensation can be used to correct for the low level of spectral overlap, by subtracting a fraction of the signal due to 488 nm excitation from the signal due to 406 nm excitation. The result of compensating the scan of FIG. 5-A is shown in FIG. 5-B.

NIH/3T3 cells were infected with MFG-vex-1 and analyzed as described in the above paragraph. Infected cells fluoresced 16 times brighter than background cells upon 406 nm excitation, and 3 times brighter than background cells upon 488 nm excitation. Uncompensated and compensated FACS scans are shown in FIGS. 5-C and 5-D, respectively.

EXAMPLE 6

NIH/3T3 cells were transfected with equal amounts of vex-1 and bex-1 at three different MOIs. Compensated dual-excitation FACS scans are shown in FIGS. 6-A, 6-B and 6-C for MOIs of 0.065, 0.13, and 0.65 for each GFP-encoding retrovirus, respectively. The scan in FIG. 6-A revealed three distinguishable cell populations: an uninfected population with low levels of fluorescence for both excitations; a population infected with vex-1, responsive to 406 nm excitation; and a population infected with bex-1, responsive to 488 nm excitation. The scan in FIG. 6-B reveals an additional "double positive" population infected with both vex-1 and bex-1, responsive to both 406 nm and 488 nm excitations. The scan in FIG. 6-C shows an increase in the double positive population, as expected from the increase in MOI. The fraction of cells in each distinguishable population in FIG. 6-C is consistent with the fraction predicted by Poisson statistics for a MOI of 0.65.

EXAMPLE 7

To evaluate the use of two reporters controlled by different regulatory elements within the same cell, BOSC 23 cells were co-transfected with four plasmids. A plasmid comprising a coding bex-1 portion controlled by a tet operator was co-transfected with a plasmid (pUHD15-1) encoding the tet transactivator, a chimera of the tet repressor and VP16 activation domain. For information on the tet transactivator, see the article by Gossen and Bujard in *PNAS USA* 89(12):5547–5551 (1992), herein incorporated by reference. In the absence of tetracyclin, bex-1 expression is induced. In the presence of tetracyclin, the tet activator dissociates from the tet operator, and transcription of bex-1 is repressed. Another plasmid comprising a coding vex-1 portion under the control of the lac operator and RSV promoter was co-transfected with a plasmid (p3'SS) constitutively expressing a modified lac repressor. For information on the modified lac repressor see the article by Fieck et al. in *Nucleic Acids Res.* 20:1785–1791 (1992), herein incorporated by reference. In the absence of IPTG, vex-1 expression is repressed. In the presence of IPTG, the lac repressor-DNA complex is disrupted, and vex-1 transcription is induced.

The BOSC 23 cells transfected with the four plasmids were divided into four populations, and the effects of inducing one, both or neither of the gfps were evaluated by adding tetracyclin and/or IPTG. FIGS. 7-A through 7-D show contour plots and histograms of dual-excitation FACS scans of the four populations. The fluorescence generated with 488 nm excitation increases only for the populations cultured under inducing conditions for bex-1 (shown in FIGS. 7-B and 7-D). The increase in 488 nm-generated fluorescence following bex-1 induction does not depend on the level of vex-1 expression, as can be seen by comparing the 488 nm histograms in FIGS. 7-B and 7-D. The fluorescence generated with 406 nm excitation increases only for the populations cultured under inducing conditions for vex-1 (shown in FIGS. 7-C and 7-D). Induction of bex-1 does not affect 406 nm-generated fluorescence, as can be seen by comparing the 406 nm histograms in FIGS. 7-C and 7-D. Simultaneous induction of bex-1 and vex-1 (FIG. 7-D) leads to increases in both 406 nm- and 488 nm-generated fluorescence.

Inducing bex-1 expression leads to approximately a 10-fold increase in the median 488 nm-generated fluorescence of the transfected population, and does not affect the 406 nm-generated fluorescence. Inducing vex-1 expression leads to approximately a 2-fold increase in the median 406 nm-generated fluorescence of the transfected population, and does not affect the 488 nm-generated fluorescence. Thus bex-1 and vex-1 can be analyzed independently by flow cytometry, and can provide simultaneous measurements of the transcriptional activities of two distinct regulatory elements.

It will be clear to one skilled in the art that the above embodiment may be altered in many ways without departing from the scope of the invention. For example, many GFP or non-GFP variants suitable for use in a method of the present invention may become available. Many analysis methods, such as high-throughput screening using fluorescence microscopy, are suitable for use with GFP mutants of the present invention. A GFP variant excited at 406 nm can be used in conjunction with the FACS-Gal assay described in the above-incorporated article by Nolan et al., or with other FACS-detectable assays measuring the production of fluorescein. Accordingly, the scope of the invention should be determined by the following claims and their legal equivalents.

What is claimed is:

1. A method of analyzing cells comprising a first transcriptional element that comprises sequences encoding a first green fluorescent protein comprising the mutations S202F, T203I, V163A, and a second transcriptional element that comprises sequences encoding a second green fluorescent protein comprising the mutations S65T, V163A, said method comprising the steps of:

illuminating a population of said cells at two wavelengths that are about 406 nm and about 488 nm, respectively; and detecting by flow cytometry at a wavelength between about 500 nm and about 540 nm first fluorescence signals from said first green fluorescent protein and second fluorescence signals from said second green fluorescent protein, wherein said first green fluorescent protein and said second green fluorescent protein are spectrally distinguishable.

2. The method of claim 1, further comprising sorting said cells by fluorescence activated cell sorting according to said first fluorescence signals and said second fluorescence signals.

3. A method of analyzing cells comprising a first transcriptional element that comprises sequences encoding a green fluorescent protein comprising the mutations S202F, T203I, V163A, and a second transcriptional element that comprises sequences encoding an enzyme which cleaves a non-fluorescent precursor to produce a fluorescent product, said method comprising the steps of:

adding said non-fluorescent precursor to said cells;

illuminating said cells at two wavelengths, one of which is substantially equal to either 406 nm or 488 nm;

detecting by flow cytometry at a wavelength between about 500 nm and about 540 nm first fluorescence signals from said green fluorescent protein; and detecting by flow cytometry second fluorescence signals from the fluorescent product of said non-fluorescent precursor, wherein said green fluorescent protein and said fluorescent product are spectrally distinguishable.

4. The method of claim 3, wherein said enzyme comprises β-galactosidase.

5. The method of claim 4, wherein said precursor comprises fluorescein-di-β-D-galactopyranosidase.

6. The method of claim 1, wherein the codons encoding said first and second green fluorescent proteins are optimized for expression in said population.

7. The method of claim 1, wherein said first and second transcriptional elements are stably integrated into a genome of said population.

8. The method of claim 1, further comprising a step of compensating said first fluorescence signals for the level of said second green fluorescent protein.

9. The method of claim 1, wherein each cell in said population contains not more than one substantially expressed said first transcriptional element and said second transcriptional element.

10. The method of claim 1, further comprising a step of exposing said population to a molecule of interest, wherein said first fluorescence signals provide a measure of an effect of said molecule of interest on expression of said first transcriptional element.

11. A method of analyzing cells comprising a transcriptional element comprising sequences encoding a green fluorescent protein comprising the mutations S202F, T203I, V163A, wherein each of said cells further comprises: a) a first protein of interest conjugated to a DNA-binding domain which binds to a regulatory element of said transcriptional element; and b) a second protein of interest conjugated to a transcription activation domain necessary for transcription of said transcriptional element, said method comprising the steps of:

illuminating said cells at a wavelength that is substantially equal to about 406 nm; and detecting by flow cytometry at a wavelength between about 500 nm and about 540 nm fluorescence signals from said green fluorescent protein, wherein fluorescence signals detected from said green fluorescent protein provides a quantitative measure of expression of said transcriptional element, and thereby provide a measure of binding of said first protein of interest to said second protein of interest.

12. The method of claim 10, wherein said first transcriptional element comprises a first regulatory element operatively connected to said sequences encoding said first green fluorescent protein and affected by said molecule of interest.

13. The method of claim 12, wherein said first regulatory element comprises a promoter.

14. A method of sorting mammalian cells comprising a first transcriptional element and a second transcriptional element, comprising the steps of:

a) measuring first fluorescence signals from a first intracellular expression product of said first transcriptional element;

b) separating into distinct populations cells expressing said first transcriptional element from cells not expressing said first transcriptional element from cells not expressing said first transcriptional element, by fluorescence activated cell sorting according to said first fluorescence signals;

c) measuring second fluorescence signals from a second intracellular expression product of said second transcriptional element; and d) separating into distinct populations cells expressing said second transcriptional element from cells not expressing said second transcriptional element, by fluorescence activated cell sorting according to said second fluorescence signals, wherein said first transcriptional element comprises sequences encoding a first green fluorescent protein comprising the mutations S202F, T203I, V163A, and said second transcriptional element comprises sequences encoding a second green fluorescent protein comprising the mutations S65T, V163A.

15. The method of claim 14 wherein each of said cells contains not more than one substantially expressed said first transcriptional element and not more than one substantially expressed said second transcriptional element.

16. A population of cells comprising:

a first transcriptional element comprising sequences encoding a first green fluorescent protein comprising the mutations S202F, T203I, V163A; and a second transcriptional element comprising sequences encoding a second green fluorescent protein comprising the mutations S65T, V163A, wherein said first green fluorescent protein is excited at a wavelength of about 406 nm, said second green fluorescent protein is excited at a wavelength of about 488 nm, and fluorescence signals from said first green fluorescent protein and said second green fluorescent proteins are detected at a wavelength between about 500 nm and about 540 nm.

17. The method of claim 1, wherein said cells are mammalian cells.

18. The method of claim 3, wherein said cells are mammalian cells.

19. The method of claim 11, wherein said cells are mammalian cells.

20. The population of claim 16, wherein said cells are mammalian cells.

* * * * *